United States Patent [19]

Yoshinaka et al.

[11] 4,048,033
[45] Sept. 13, 1977

[54] PROCESS FOR PREPARING PERCHLOROMETHYLBENZENE

[75] Inventors: Shigeo Yoshinaka; Seiji Uchiyama; Masaharu Dōya, all of Niigata, Japan

[73] Assignee: Mitsubishi Gas Chemical Company, Inc., Tokyo, Japan

[21] Appl. No.: 504,989

[22] Filed: Sept. 10, 1974

[30] Foreign Application Priority Data

Sept. 10, 1973 Japan .................................. 48-101814

[51] Int. Cl.$^2$ ................................................ B01J 1/10
[52] U.S. Cl. ............................ 204/158 HA; 204/163 R
[58] Field of Search ..................... 204/158 HA, 163 R

[56] References Cited

U.S. PATENT DOCUMENTS 2,810,688  10/1957  Ivins et al. ............................ 204/163

FOREIGN PATENT DOCUMENTS 17,262  8/1964  Japan ............................ 204/158 HA Primary Examiner—Howard S. Williams Attorney, Agent, or Firm—Wenderoth, Lind & Ponack

[57] ABSTRACT

A process for producing perchloromethylbenzene by reacting a methylbenzene selected from the group consisting of compounds of the formula

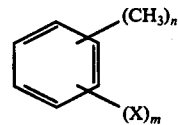

wherein
X is a chlorine or bromine atom, $m$ is a number of 0, 1 or 2, and $n$ is an integer of 1 to 3, and compounds of the above formula wherein the side chain methyl group is partially chlorinated, with chlorine under the irradiation of light containing ultraviolet rays, characterized in that the reaction is carried out in the presence of said perchloromethylbenzene in the reaction system as a solvent.

11 Claims, No Drawings

PROCESS FOR PREPARING PERCHLOROMETHYLBENZENE

This invention relates to a process for preparing perchloromethylbenzene.

Methods for chlorinating the pendant methyl group of methylbenzene which have previously been practised include, for example, a method in which the chlorination reaction is carried out under the irradiation of light, or a method in which benzoyl peroxide, azobisisobutyronitrile or a peroxide is added to the reaction mixture, and chlorine is mixed or bubbled in the liquid phase. In such methods, however, a compound containing chlorine directly substituted at the benzene nucleus and a tarry material are formed as by-products, and chlorinating decomposition or coloration is often seen to take place. Thus, these methods present a number of difficulties. For example, the yield of the product is reduced, or the reaction requires a long period of time or further, the quality and purity of the product are adversely affected. These difficulties are especially marked in the production of $\alpha, \alpha, \alpha, \alpha', \alpha', \alpha'$-hexachloro-p-xylene or $\alpha, \alpha, \alpha, \alpha', \alpha', \alpha'$-hexachloro-m-xylene. Above all, they are most marked in the production of the above m-xylene. Accordingly, commercial production of these compounds have encountered many difficulties.

As a method for inhibiting such side reactions and eliminating the other various defects, it has been known to add an alkylene polyamine, benzamide, urea, acetamide, a triaryl phosphate or sorbitol to the reaction mixture. Such a method is not entirely satisfactory because of the low yield, quality and purity of the product and the high cost of the additives used.

It has also been known to use a polychlorinated hydrocarbon such as carbon tetrachloride, chloroform, dichlorobenzene or trichlorobenzene, as a reaction solvent in order to inhibit the formation of a by-product in which chlorine is directly attached to the nucleus. However, when a solvent having a relatively low boiling point, such as carbon tetrachloride, is used, the vapor pressure of the solvent at the temperature of the reaction is high, and the reaction solvent is carried away out of the reaction system by being entrained with the hydrogen chloride gas formed. Furthermore, when a solvent having a high boiling point such as trichlorobenzene is used, it is difficult to separate the solvent from the resulting perchlorinated methylbenzene, and an enormous amount of energy must be consumed.

The inventors made extensive investigations in order to find a method for perchlorinating the side chain methyl group of methylbenzene with commercial advantage. Consequently, they found that when the initial stage of the reaction, i.e. the stage of introducing several chlorine atoms into the side chains of the starting methylbenzene molecule is performed in a system where the objective perchlorinated methylbenzene is present as a solvent, the intended perchlorinated methylbenzene can be obtained in a high yield within short periods of time without the formation of by-products such as a nuclearly chlorinated compounds or a tarry material, the loss of solvent, and the need to separate and recover the solvent in the purification of the reaction product, while shortening the time required for the reaction. The term "several chlorine atoms" to be introduced into the side chains of the starting methylbenzene molecule at the initial stage of reaction is used herein to mean such a number of chlorine atoms that corresponds to one chlorine atom per side chain methyl group.

According to this invention, there is provided a process for producing perchloromethylbenzene by reacting a methylbenzene selected from the group consisting of compounds of the formula

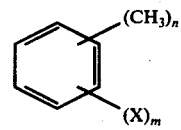

wherein

X is a chlorine or bromine atom, $m$ is a number of 0, 1 or 2, and $n$ is an integer of 1 to 3, and compounds of the above formula wherein the side chain methyl group is partially chlorinated, with chlorine under the irradiation of light containing ultraviolet rays, characterized in that the reaction is carried out in the presence of said perchloromethylbenzene in the reaction system as a solvent.

The process of this invention will be described below in greater detail.

The compounds used as a starting material in the process of this invention include 1. compounds of the formula

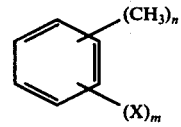

wherein

X is a chlorine or bromine atom, $m$ is a number of 0, 1 or 2, and $n$ is an integer of 1 to 3, and 2. Compounds of the above formula in which the side chain methyl group is partially chlorinated.

Examples of the compounds (1) are toluene, xylene, mesitylene, pseudocumene, and halogenated derivatives thereof such as para-chlorotoluene.

In the present application, the above compounds (1) and (2) are generically referred to as methylbenzene.

The compounds (2) are compounds in which the pendant methyl group has not been perchlorinated, but partially chlorinated. The term "perchlorination" means that when chlorinating the side chain methyl group, the maximum number of chlorine atoms are introduced into the side chain. Furthermore, the term "perchloromethylbenzene" as a final compound obtained in this invention means a compound in which the maximum number of chlorine atoms have been introduced to the side chain of the starting methylbenzene.

When the number of methyl groups of the methyl benzene is 1 to 3, perchlorination is theoretically shown as follos:

$$Ar(CH_3)_n + 3nCl_2 \rightarrow Ar(CCl_3)_n + 3nHCl$$

wherein

Ar is a benzene nucleus or a benzene nucleus substituted by a halogen atom, and $n$ is an integer of 1 to 3.

In the above reaction, not all of the hydrogen atoms of the side chain methyl groups are actually replaced by chlorine as a result of chlorination. For example, in the case of a compound in which two methyl groups are present at adjacent positions, such as o-xylene, the maximum number of chlorine atoms that can be introduced into the side chain as a result of chlorination is 5, as shown by the following formula

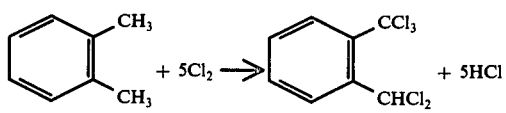

Accordingly, in this case, a compound in which five chlorine atoms have been introduced to the side chain methyl groups is what is called perchloromethylbenzene in the present invention. In the case of trimethylbenzene in which the methyl groups are present in adjacent positions, a compound in which 5 chlorine atoms are introduced to two adjacent methyl groups is perchloromethylbenzene.

When a compound having methyl groups at adjacent positions is perchlorinated, an attempt to shorten the reaction time by elevating the reaction pressure may sometimes result in side-reactions such as partial chlorinating decomposition. Therefore, the process of this invention is especially effective for compounds in which the methyl groups are not present at adjacent positions, such as m-xylene, p-xylene, p-chlorotoluene or mesitylene.

The characteristic feature of the present invention resides in that in the synthesis of perchlorinated methylbenzene by reacting methylbenzene with chlorine under the irradiation of light containing ultraviolet rays, the intended compound, that is to say, perchlorinated methylbenzene, is present in the reaction system as a solvent whereby the perchlorination of the starting methylbenzene is carried out. The present invention is characterized specifically in that the initial stage of reaction, where the several chlorine atoms are introduced into the side chains of the starting methylbenzene molecule (for instance, in the formation reaction of monochlorocompounds or dichloro compounds in the case of xylene), is conducted in a system where the objective perchlorinated methylbenzene is present as a solvent. When the initial stage of reaction is carried out in such a system where perchlorinated methylbenzene is present as a solvent, the intended perchlorination reaction proceeds very smoothly and selectively whereby undesired side reactions such as the formation of a nuclearly chlorinated compound or tarry material, etc., are effectively inhibited.

It is well known that principal by-products in the formation reaction of perchlorinated methylbenzene are compounds such as a nuclearly chlorinated compound, tarry materials, etc., and it is also known well that a certain type of solvent is effective to inhibit the formation of such by-products.

As the results of intensive studies on the formation of those by-products as well the influence exerted thereon by a solvent, the inventors of this invention have found surprisingly that the formation of by-products is most likely to take place at the initial stage of reaction where several chlorine atoms are introduced into the side chains of the starting methyl benzene, and that when said initial stage of reaction is performed in such a system where the object perchlorinated methylbenzene is present as a solvent, the formation of by-products is effectively eliminated.

The inventors likewise have found that whereas the perchlorinated methylbenzene (for example, hexachloro compounds in the case of xylene) has a remarkable effect to of inhibiting the formation of by-products, intermediate products formed during the formation of perchlorinated methylbenzene from methylbenzene (for example, even pentachloro compounds in the case of xylene) do not in the least have such effect as a solvent to inhibit the formation of by-products. This means that when the initial stage of reaction of introducing several chlorine atoms into the side chains of the starting methylbenzene is conducted in such a system where these intermediate products are present in a predominant amount, there is a larger quantity of by-products formed. In order to stably avoid the formation of by-products, therefore, it is essentially required that perchlorinated methylbenzene be present in the reaction system as a solvent in not less than a predetermined concentration.

The process of this invention can be performed either batchwise or continuously.

The amount of perchloromethylbenzene to be present as a solvent in the reaction system from the start of the reaction is 0.3 to 15 times, preferably 0.8 to 5 times, the weight of the starting methylbenzene in the case of a batchwise operation. In the case of a continuous operation, it is difficult to specify the amount of the perchloromethylbenzene solvent on the basis of the weight of the starting methylbenzene. Accordingly, in the case of the continuous operation, it is necessary to feed the starting methylbenzene continuously while maintaining the concentration of the perchloromethylbenzene in the reaction mixture at 40 to 99% by weight.

The reaction temperature in the process of this invention is generally 50° to 180° C. But in order to shorten the reaction time and inhibit side-reactions to increase the yield of the final product, temperatures of 100° to 160° C. are preferred.

The chlorine may be used in a large excess in the case of batchwise operation, but the sufficient amount is at least 110% of the theoretical amount. Usually, amounts of 110 to 120% are sufficient. In the case of the continuous operation, it is not altogether necessary to add chlorine in excess.

Preferably, the process of this invention is performed in a dry condition.

In the process of this invention, it is not altogether necessary to add a substance for inhibiting any adverse effect that may occur as a result of the incorporation of catalysts or metal compounds, such as benzaldehyde, acetamide, N,N-dimethyl formamide, an alkylene polyamine, urea, a triaryl phosphate or sorbitol, to the reaction mixture. But if desired, it is possible to add these substances.

According to a preferred embodiment of performing the process of this invention batchwise, when the starting methylbenzene is mixed with 0.3 to 15 times, preferably 0.8 to 5 times, its weight of perchloromethylbenzene, and chlorine is gradually introduced into the mixture while maintaining the reaction temperature at 100° to 160° C. and under the irradiation of light containing ultraviolet rays, the reaction proceeds soon after the introduction of chlorine while evolving hydrogen chloride vigorously. At this time, it is preferred that the reaction is carried out while adjusting the amount of chlorine introduced so that a large quantity of chlorine is not lost from the gas exhaust port and to such an extent that the reaction temperature can be maintained at a predetermined point. Furthermore, it is preferred to carry out the reaction while maintaining the reaction temperature by such a method as heating or cooling the reaction mixture during the reaction. Usually, at an initial stage of the reaction, the rate of reaction is extremely substantial, and high heat is generated. Therefore, in order to remove the heat of reaction, the reaction mixture needs to be cooled. After that, the rate of reaction decreases gradually and the temperature decreases accordingly. Thus, in order to maintain the reaction temperature at a predetermined point, heating becomes necessary. With a decrease in the rate of reaction, the absorption of chlorine is scarcely observed, at which time the reaction is terminated.

According to one preferred embodiment of performing the process of this invention continuously, perchloromethylbenzene is present in a reactor in advance, and while maintaining the reaction temperature at a predetermined point, methylbenzene as a starting material is continuously introduced. At this time, while maintaining the concentration of the perchloromethylbenzene at 40 to 99% by weight, the methylbenzene is reacted with chlorine under the irradiation of light containing ultraviolet rays, and the reaction mixture is continuously withdrawn. When it is desired to carry out the reaction while maintaining the concentration of the perchloromethylbenzene at a relatively high level, one reactor may suffice. However, when it is desired to maintain the concentration of the perchloromethylbenzene at a relatively low level, it is preferred to use two or more reactors connected in series.

In an embodiment in which the process of this invention is performed continuously using two or more reactors connected in series, another reactor is preferably positioned before a main reactor in which the concentration of the perchloromethylbenzene is maintained at 40 to 99% by weight in order to increase the utilization of chlorine introduced, whereby the starting material and the gas exhausted from the main reactor are fed into the other reactor and reacted with chlorine contained in the introduced gas under the irradiation of light, and the reaction mixture withdrawn from the other reactor is then introduced into the main reactor.

However, if the degree of chlorination at the reactor positioned before the main reactor (to be referred to as a pre-reactor) is increased, the amounts of nuclearly chlorinated by-products and tarry material formed necessarily increase. Therefore, it is desirable to adjust the degree of chlorination in the pre-reactor to a low level and introduce the reaction mixture of a low degree of chlorination into the main reactor. In order to adjust the amounts of the nuclearly chlorinated by-products and tarry material to a low level and to increase the yield of the final product, it is advisable to adjust the average degree of chlorination of the side chain methyl groups in the pre-reactor so that the average number of chlorine atoms introduced into one molecule of the starting methylbenzene is not more than 2. The reaction to be carried out in the pre-reactor under these conditions is one in which the chlorination does not substantially afford perchloromethylbenzene, but gives a compound in which the side chain of the starting methylbenzene is partially chlorinated.

According to another preferred embodiment of continuously performing the process of this invention, perchlorination is carried out in two or more reactors connected in series. This continuous process will be described below with reference to an example in which two reactors are connected in series, and a greater part of perchlorination is effected in a first reactor, and the perchlorination is completed in a second reactor.

The starting methylbenzene is continuously fed into a first reactor in the form of a liquid. An overflowing port is provided at a suitable height in the first reactor. The reaction mixture overflows from the overflowing port according to the rate of its formation, and is thus fed to a second reactor. Chlorine gas is partly introduced into the bottom of the second reactor, but a greater part of it, into the first reactor at its bottom. The exhaust gas from the second reactor may be removed out of the system, but it can also be introduced into the liquid in the first reactor. The rate of feeding the starting methylbenzene into the first reactor and the rate of feeding chlorine into the first reactor are adjusted so that the reaction mixture contains perchloromethylbenzene in a concentration of 40 to 99% by weight. The amount of the chlorine gas to be fed into the second reactor is adjusted according to the composition of the reaction mixture fed from the first reactor to the second reactor. When the concentration of the perchloromethylbenzene in the reaction mixture to be fed into the second reactor is high, the amount of chlorine to be fed is decreased, and when the concentration of the perchloromethylbenzene is low, the amount of chlorine to be fed is increased. The size of the second reactor is preferably determined according to the concentration of the unreacted intermediate in the reaction mixture. If the size of the second reactor is larger than necessary, the residence time of the liquid becomes larger than necessary.

The process mentioned above in which perchlorination is carried out in two or more reactors connected in series has various advantages such as the ease of controlling the reaction, more effective inhibition of the formation of by-products detrimental to the reaction, and the increased utilization of chlorine. Thus, this embodiment is preferred for performing the process of this invention.

Perchlorination can also be carried out in three or more reactors, but this does not afford particular advantages over the case of using two reactors. Rather, it is disadvantageous because of the increased cost of providing the reactors. However, an embodiment in which the process of this invention is performed using a pre-reactor and a first reactor and a second reactor for performing perchlorination as a main reactor is very much preferred in this invention.

According to this invention, perchloromethylbenzene of a high concentration can be obtained in a high yield with reduced amounts of the nuclearly chlorinated compound or tarry material as by-products. Furthermore, since the reaction mixture does not contain a different kind of solvent, the removal and recovery of the solvent after driving off the chlorine is not necessary, but the product can be directly purified by ordinary methods such as distillation or recrystallization to afford the final product easily.

Accordingly, no measure is required to prevent the loss of solvent as in the case of using carbon tetrachloride as the solvent, nor is it necessary to perform an operation of separating and recovering the solvent. Furthermore, the reaction time can be shortened.

The following Examples illustrate the present invention. Examples 1 to 7 illustrate the process of the present invention performed batchwise, and Examples 8 to 12, the process of this invention performed continuously.

EXAMPLE 1

A 500 ml. reactor equipped with a thermometer, a stirrer, a chlorine blow inlet tube and a reflux condenser which was adapted to act concurrently as an exhaust port was charged with 127.4g (1.2 mols) of m-xylene and 200.0 g of $\alpha,\alpha,\alpha,\alpha',\alpha',\alpha'$-hexachloro-m-xylene. The contents were heated to 120° C., and dry chlorine was blown into the reactor under the irradiation of light using a high pressure mercury lamp. Soon after the blowing of chlorine, there was a rise in the reaction temperature along with the evolution of hydrogen chloride. Chlorine was continuously introduced under the irradiation of light while maintaining the reaction temperature at 130° C. The amount of chlorine blown was 1.3 mols/hour for the first 5 hours, and after the lapse of 5 hours, the amount of chlorine was somewhat decreased. The reaction was performed for 8 hours. The amount of chlorine used was 118% of theory.

After the reaction, air was blown into the reactor while the reaction mixture was maintained at 100 to 120° C. to drive off chlorine dissolved therein. The reaction mixture was distilled at reduced pressure to afford 568 g of a colorless transparent fraction having a boiling point of 135° to 140° C./2-3 mmHg. Gas-chromatographic analysis of this fraction showed that it is nearly pure $\alpha,\alpha,\alpha,\alpha',\alpha',\alpha'$-hexachloro-m-xylene. Hydrolysis of this fraction afforded terephthalic acid in a yield almost close to the theoretical value.

Supposing that the amount of freshly formed $\alpha,\alpha,\alpha,\alpha',\alpha',\alpha'$-hexachloro-m-xylene is obtained by subtracting 200 g (initially added $\alpha,\alpha,\alpha,\alpha',\alpha',\alpha'$-hexachloro-m-xylene) from that of the above fraction, the yield of $\alpha,\alpha,\alpha,\alpha',\alpha',\alpha'$-hexachloro-m-xylene is 98.0% based on the m-xylene.

REFERENCE EXAMPLE 1

Using the same reactor as used in Example 1, 127.4 g (1.2 mols) of m-xylene and 300 g of carbon tetrachloride were placed in it, and heated to 70° C. Then, m-xylene was reacted for 4 hours at 70° to 80° C. while introducing dry chlorine at a rate of 1.2 mols/hour under the irradiation of light. During this time, the reaction mixture was cooled by passing a cooling liquid kept at −10° C. through the reflux condenser to prevent the loss of the solvent as much as possible. After performing the reaction for 5 hours, the cooling of the reflux condenser was stopped, and while distilling off carbon tetrachloride, the reaction was performed at 80 to 100° C. for 5 hours, and then for 3 hours at 130° C. while introducing chlorine at a rate of 1.2 mols/hour. The amount of the carbon tetrachloride recovered was 288 g. The reaction mixture was treated in the same way as in Example 1 to afford 313.5 g of a fraction having a boiling point of 135° to 143° C./2-3 mmHg. The yield of this fraction was 83.5% as $\alpha,\alpha,\alpha,\alpha',\alpha',\alpha'$-hexachloro-m-xylene based on the m-xylene charged.

REFERENCE EXAMPLE 2

Using the same reactor as used in Example 1, the reaction was performed for 14 hours in the same way as in Example 1 except that the reactor was charged with 169.8 g (1.6 mols) of m-xylene, but $\alpha,\alpha,\alpha,\alpha',\alpha',\alpha'$-hexachloro-m-xylene was not added.

After the reaction, the chlorine dissolved in the reaction mixture was driven off. The reaction mixture was then distilled at reduced pressure to afford 402.0 g of a fraction having a boiling point of 135° to 145° C. The yield of this fraction was 80.3% as $\alpha,\alpha,\alpha,\alpha',\alpha',\alpha'$-hexachloro-m-xylene based on the m-xylene charged. A large amount of the tarry material was seen to remain in the distillation still.

EXAMPLE 2

The same reactor as used in Example 1 was charged with 106.2 g (1.0 mol) of p-xylene, 210.0 g of $\alpha,\alpha,\alpha,\alpha',\alpha',\alpha'$-hexachloro-p-xylene and 0.2 g of benzamide, and the contents were heated to 120° C. Then, chlorine was blown into the reactor under the irradiation of light. Soon after the blowing of chlorine, there was a rise in the reaction temperature along with the evolution of hydrogen chloride. The reaction was performed at 130° C. under the irradiation of light while continuing the introduction of chlorine. The amount of chlorine blown was 1.08 mols/hour for the first 5 hours, and after the lapse of 5 hours, the amount of chlorine was somewhat decreased. In this way, the reaction was continued for 8 hours. The total amount of chlorine was 115% of theory.

After the reaction the chlorine dissolved in the reaction mixture was driven off. The reaction mixture was distilled at reduced pressure to afford 517.2 g of a fraction having a boiling point of 140 to 144° C/5 mmHg. When the fraction was cooled, it become white crystals having a melting point of 107.5° to 109.5° C. Gas-chromatographic analysis of this product showed that it consisted almost solely of pure $\alpha,\alpha,\alpha,\alpha',\alpha',\alpha'$-hexachloro-p-xylene. Hydrolysis of this product gave terephthalic acid almost in a theoretical yield. Supposing that the amount of freshly formed $\alpha,\alpha,\alpha,\alpha',\alpha',\alpha'$-hexachloro-p-xylene is obtained by subtracting the amount of the initially charged $\alpha,\alpha,\alpha,\alpha',\alpha',\alpha'$-hexachloro-p-xylene from that of the above fraction, the yield of the product is 98.2% based on the charged p-xylene.

REFERENCE EXAMPLE 3

The same reactor as used in Example 1 was charged with 127.4 g (1.2 mols) of p-xylene, 280 g of carbon tetrachloride and 0.2 g benzamide, and the reaction was performed at 70° to 80° C. for 5 hours while passing chlorine under the irradiation of light. Then, while distilling off carbon tetrachloride, the reaction was further carried out at 80° to 100° C. for 5 hours, and at 130° C. for 3 hours. All during this time, chlorine was introduced at a rate of 1.2 mols/hour. The reaction mixture was treated in the same way as in Example 1, and distilled at reduced pressure to afford 330 g of a fraction having a boiling point of 140° to 145° C./5 mmHg. The yield of this fraction was 87.9% calculated as $\alpha,\alpha,\alpha,\alpha',\alpha',\alpha'$-hexachloro-p-xylene.

EXAMPLE 3

The same reactor as used in Example 1 was charged with 129.0 g (1.4 mols) of toluene, 260 g of benzotrichloride, and 0.4 g of N,N-dimethyl formamide, and while introducing chlorine at a rate of 1.4 mols/hour under the irradiation of light, the reaction was performed at 100° to 110° C. for 2.5 hours, and at 130° to 135° C. for 2.5 hours. After the reaction, the chlorine dissolved in the reaction mixture was driven off, and the reaction mixture was distilled at reduced pressure to afford 524.6 g of a fraction having a boiling point of 94° to 97° C. Gas-chromatographic analysis of this fraction showed that it consisted almost solely of benzotrichloride. Hydrolysis of it afforded benzoic acid almost in a theoretical yield. Supposing that the amount of the freshly formed benzotrichloride is obtained by substracting the amount of the benzotrichloride initially added from that of the above fraction, the yield of benzotrichloride based on the toluene charged is 96.7%.

EXAMPLE 4

The same reactor as used in Example 1 was charged with 120.2 g (1.0 mol) of mesitylene, 200 g of 1,3,5-tris(-trichloromethyl)benzene and 0.3 g of N,N-dimethyl formamide, and while maintaining the contents at 140° C. under the irradiation of light, dry chlorine was introduced into the reactor. The reaction was performed under these conditions for 12 hours. After driving off the dissolved chlorine, the reaction mixture was cooled to afford 623 g of yellow crystals. A part of the crystals was withdrawn and converted to its methyl ester by the method disclosed at page 322 of J. Appln. Chem. 4(1954). Gas-chromatographic analysis of the methyl ester showed that it consisted almost solely of trimethyl trimesate. Supposing that the amount of the freshly formed 1,3,5-tris(trichloromethyl)benzene is obtained by subtracting 200 g [the amount of the initially charged 1,3,5-tris(trichloromethyl) benzene] from that of the above crystals, the yield of this product is 98.3% based on the charged mesitylene.

EXAMPLE 5

The same reactor as used in Example 1 was charged with 126.6 g (1.0 mols) of p-chlorotoluene, 300.0 g of p-chlorobenzotrichloride and 0.5 g of benzamide, and while introducing chlorine at a rate of 1.0 mol/hour, the reaction was performed for 6 hours at 150° C. under the irradiation of light. After the reaction, the chlorine dissolved in the reaction mixture was driven off, and the reaction mixture was distilled at reduced pressure to afford 521.6g of a fraction having a boiling point of 108° to 112° C./10 mmHg. Gas-chromatographic analysis of this fraction showed that it consisted almost solely of pure p-chlorobenzotrichloride. Supposing that the amount of the freshly formed p-chlorobenzotrichloride is obtained by subtracting the amount of the initially charged p-chlorobenzotrichloride from that of the above fraction, the yield of this product based on the charged p-chlorotoluene is 96.4%.

EXAMPLE 6

The same reactor as used in Example 1 was charged with 124.4 g (1.2 mols) of o-xylene, 300.0 g of $\alpha,\alpha,\alpha,\alpha'\lambda,\alpha'$-pentachloro-o-xylene and 0.5 g of benzamide, and the reaction was performed for 8 hours at 110° C. while introducing chlorine at a rate of 1.2 mols/hour under the irradiation of light.

After the reaction, the chlorine dissolved in the reaction mixture was driven off to obtain 629.5 g of a chlorinated product. Analysis of this product by gas-chromatography showed that the concentration of $\alpha,\alpha\lambda,\alpha,\alpha',\alpha'$-pentachloro-o-xylene was 95.2%. Supposing that the initially charged $\alpha,\alpha,\alpha\alpha',\alpha'$-pentachloro-o-xylene remained as it was, the amount of this xylene was subtracted, and the remainder was regarded as the freshly formed $\alpha,\alpha,\alpha,\alpha',\alpha'$-pentachloro-o-xylene, the yield of the freshly formed $\alpha,\alpha,\alpha,\alpha',\alpha'$-pentachloro-o-xylene being 89.6%.

EXAMPLE 7

The same reactor as used in Example 1 was charged with 127.4 g (1.2 mols) of m-xylene and 200.0 g of the reaction mixture obtained by the same procedure as in Example 1, and the reaction was performed by the same procedure as in Example 1. After the reaction, the chlorine dissolved in the reaction mixture was driven off to afford 573.2 g of a chlorinated product. Gas-chromatographic analysis of this product showed that the concentration of $\alpha,\alpha,\alpha,\alpha',\alpha',\alpha'$-hexachloro-m-xylene was 97.9%.

EXAMPLE 8

In this Example, the process of this invention was performed continuously using one reactor.

A 2-liter glass flask equipped with a light irradiating device, a thermometer, a stirrer, a reflux condenser, a chlorine blow inlet, a feed inlet for m-xylene and an opening for overflowing the reaction mixture was charged with 956 g of m-xylene, and heated to elevate the temperature of the contents of 135° C. Then, while blowing chlorine into the flask at a rate of about 636 g/hour, the reaction was performed for 9 hours with stirring under the irradiation of light. The irradiation of light was performed using a high pressure mercury lamps. After performing the chlorination for 9 hours, the reaction mixture contained about 87% by weight of $\alpha,\alpha,\alpha,\alpha',\alpha',\alpha'$-hexachloro-m-xylene.

While maintaining the temperature of the resultant reaction mixture at 135° C. and stirring the mixture under the irradiation of light, m-xylene and chlorine were continuously fed into the flask at a rate of about 81 g/hour (0.76 mol/hour) and about 390 g/hour (5.50 mols/hours), respectively, to perform the reaction. Prior to being fed to the flask, the m-xylene had been preheated to 120° to 130° C. Chlorine was bubbled to the bottom of the reactor in the gaseous state. The gas which was released from the flask was thoroughly cooled via the condenser, and then led to the outside of the reaction system from the top of the condenser. The reaction mixture which increased in amount as a result of feeding and reacting the m-xylene was removed out of the reaction system by overflowing from the overflowing opening. In this Example, the volume of the reaction was about 1.6 liters when the liquid was filled up to the overflowing opening. The reaction mixture which overflowed from the reactor was conducted to the top of a chlorine gas-removing tower, and contacted countercurrently with nitrogen gas to remove the chlorine dissolved therein. Then, it was conducted to a reservoir for the reaction mixture.

After performing the reaction in this way for 48 hours, the reaction mixture was analyzed by gas-chromatography, and it was found that the reaction mixture consisted of 95.2% by weight of $\alpha,\alpha,\alpha,\alpha',\alpha',\alpha'$-hexachloro-m-xylene, 0.6% by weight of a chlorinated intermediate formed during conversion of m-xylene to $\alpha,\alpha,\alpha,\alpha',\alpha',\alpha'$-hexachloro-m-xylene, and 4.2% by weight of other compounds. When the reaction was performed for an additional 20 hours, 1624 g (15.30 mols) of m-xylene and 7796 g (109.9 mols) of chlorine were fed into the reactor during this period, and 4781 g of the reaction mixture was obtained. Its gas-chromatographic analysis showed that the reaction mixture consisted of 95.4% by weight of $\alpha,\alpha,\alpha,\alpha',\alpha',\alpha'$-hexachloro-m-xylene, 0.7% by weight of a chlorinated intermediate and 3.9% by weight of other compounds. Analysis showed that the amount of the $\alpha,\alpha,\alpha,\alpha',\alpha',\alpha'$-hexachloro-m-xylene formed was 4561 g (14.58 mols), and this corresponded to a yield of 95.3 % based on the m-xylene.

EXAMPLE 9

In this Example, the perchlorination reaction was carried out in two reactors.

The first reactor (main reactor) was the same as that used in Example 8, and a second reactor (500 ml. glass reactor to be referred to as a rear reactor) equipped with a light irradiating device, a thermometer, a reflux condenser, a gas blow inlet, a liquid feed opening and a reaction mixture overflow opening was disposed at a position lower than that of the main reactor. The volume of the rear reactor was 300 ml. when it was filled up to the overflow opening. The overflow opening of the main reactor was connected to the liquid feed opening of the rear reactor, and a pipe was provided so that the reaction mixture overflow from the overflowing opening of the rear reactor was conducted to the top of a chlorine gas-removing tower as in Example 8.

The final reaction mixture obtained in Example 8 was filled in the main reactor, and then heated to 135° C. When the temperature of the reaction mixture reached 135° C., about 81 g/hour (0.76 mol/hour) of m-xylene and about 338 g/hour (4.77 mols/hour) of chlorine were continuously fed into the main reactor under irradiation of light with stirring. The m-xylene was pre-heated to 120° to 130° C. prior to being fed to the reactor. Chlorine in the gaseous form was bubbled to the bottom of the reactor. The gas that was released from the reactor was conducted to the outside of the reaction system from the top of the condenser. The reaction mixture which increased in amount as a result of feeding and reacting the m-xylene that overflowed was conducted to the rear reactor. When the rear reactor was filled with the reaction mixture from the main reactor, the temperature of the contents was raised to 130° C. Then the reaction was performed at this temperature under the irradiation of light while continuously blowing chlorine at a rate of about 30 g/hour (0.42 mol/hour). The reaction mixture that left the rear reactor was conducted to the reservoir after removing chlorine dissolved therein, as in Example 8.

After performing the reaction in this way for 48 hours, the reaction mixture was analyzed and found to have the composition shown in Table 1.

In the same way, the reaction was performed for an additional 20 hours. During this time, 1625 g (15.30 mols) of m-xylene was fed to the reactors. Chlorine was fed in an amount of 6736 g to the main reactor and in an amount of 586 g (8.26 mols) to the rear reactor during this time. Thus, after removing dissolved chlorine, 4758 g of the reaction mixture was obtained. The reaction mixture in the main reactor and the final reaction mixture at the end of the additional 20 hours, were analyzed, and the results are shown in Table 2.

Table 1

| | Reaction mixture obtained after 48 hours reaction | |
|---|---|---|
| | Main reactor | Rear reactor |
| m-Xylene | 0.02 wt.% | — |
| α-Chloro-m-xylene | 0.3 | — |
| α,α'-Dichloro-m-xylene | 0.8 | — |
| α,α,α'-Trichloro-m-xylene | 1.9 | — |
| α,α,α',α'-Tetrachloro-m-xylene | 5.4 | — |
| α,α,α',α'-Pentachloro-m-xylene | 9.3 | — |
| α,α,α',α',α'-Hexachloro-m-xylene | 78.5 | 96.3 wt.% |
| Other compounds* | 3.3 | 2.9 |

*The other compounds consisted mainly of a nuclearly chlorinated compound and a tarry material.

Table 2

| | Reaction mixture in main reactor at end of 68 hours | Final reaction mixture obtained after 68 hours |
|---|---|---|
| m-Xylene | 0.02 wt.% | — |
| α-Chloro-m-xylene | 0.3 | — |
| α,α'-Dichloro-m-xylene | 0.8 | — |
| α,α,α'-Trichloro-m-xylene | 1.8 | — |
| α,α,α',α'-Tetrachloro-m-xylene | 5.2 | — |
| α,α,α,α',α'-Pentachloro-m-xylene | 9.4 | — |
| α,α,α,α',α'-Hexachloro-m-xylene | 79.2 | 97.1 wt.% |
| Other compounds * | 3.3 | 2.9 |

* Same as the footnote to Table 1.

According to the results of analysis, the final reaction mixture obtained at the end of the additional 20 hours contained 4620 g of α,α,α,α',α',α'-hexachloro-m-xylene which corresponded to a yield of 96.5% based on the m-xylene.

REFERENCE EXAMPLE 4

Four reactors (500 ml. glass flasks) each equipped with a light irradiating device, a thermometer, a stirrer, a reflux condenser, a chlorine gas blow inlet, a liquid feed opening and a liquid overflow opening were positioned stepwise with each of them being at a different height. The overflow opening of the reactor at the highest position was connected to the liquid feed opening of the next reactor, and the overflow opening of this second highest reactor, to the liquid feed opening of the third reactor. The overflow opening of the third reactor was connected to the liquid feed opening of the lowest reactor. The overflow opening of the lowest reactor was connected to the top of a chlorine gas-removing tower. The volume of each of the reactors was about 380 ml. when filled up to the overflow opening.

The first reactor situated at the highest position was charged with m-xylene, and heated to 130° C. At this temperature, m-xylene and chlorine were continuously fed at a rate of about 88 g/hour and about 283 g/hour, respectively, and the reaction was performed with stirring under the irradiation of light. The reaction mixture that overflowed from the first reactor was conducted to the second reactor. When the second reactor was filled with the liquid, the inside of the reactor was elevated to 130° C., and the reaction was performed under the irradiation of light while introducing chlorine at a rate of 141 g/hour. Similarly, the temperature of the inside of each of the third and fourth reactors was mantained at 130° C., and the reaction was performed under the irradiation of light while introducing chlorine continuously at a rate of 6 g/hour and 40 g/hour respectively. The reaction mixture that overflowed from the fourth reactor was conducted to a chlorine-removing tower and contacted countercurrently with nitrogen gas. Then, it was conducted to a reservoir for the reaction mixture.

The reaction was performed for 60 hours by this method, and a sample was collected from each of the reactors, and analyzed by gas-chromatography. The results are shown in Table 3.

The reaction was performed for an additional 24 hours. During this time, 2109 g of m-xylene was fed, and 6193 g of the final reaction mixture which left the chlorine-removing tower was obtained.

Analysis of the final reaction mixture showed that it consisted of 70.7% by weight of α,α,α,α',α',α'-hexachloro-m-xylene and 29.3% by weight of other compounds. According to the results of analysis, 4378 g of α,α,α,α',α',α'-hexachloro-m-xylene was formed during the period of 24 hours after 60 hours, and this corresponded to a yield of 70.3% based on the m-xylene.

This Reference Example 4 shows that since in the first reactor, considerable amounts of substances (nuclearly chlorinated compound and tarry material) detrimental to the reaction were already formed, and they were brought to the second and following reactors, the final yield of the product was kept at a low value.

Table 3

| Composition of the reaction mixture in each reactor | | | | |
| --- | --- | --- | --- | --- |
| | 1st reactor | 2nd reactor | 3rd reactor | 4th reactor |
| m-Xylene | 0.6 wt.% | — | — | — |
| α-Chloro-m-xylene | 1.6 | — | — | — |
| α,α-Dichloro-m-xylene | 0.5 | — | — | — |
| α,α'-Dichloro-m-xylene | 4.3 | 0.2 wt.% | — | — |
| α,α,α'-Trichloro-m-xylene | 10.4 | 0.9 | — | — |
| α,α,α',α'-Tetrachloro-m-xylene | 19.2 | 5.7 | 0.6 wt.% | — |
| α,α,α',α',α'-Hexachloro-m-xylene | 20.8 | 51.5 | 70.7 | 69.7 wt.% |
| Others* | 20.8 | 25.0 | 25.2 | 30.3 |

*Same as the footnote to Table 1.

EXAMPLE 10

In this Example, the process of this invention was performed using one pre-reactor and two reactors for performing perchlorination as a main reaction.

Three glass reactors (1 liter, 2 liter and 500 ml. flasks, respectively) each equipped with a light irradiating device, a thermometer, a stirrer, a reflux condenser, a gas blow inlet, a liquid feed inlet and a liquid overflow opening were positioned stepwise in the order of the 1-liter reactor, 2-liter reactor and 500 ml. reactor at different levels (these reactors will be referred to as a pre-reactor, a main reactor and a rear reactor in this order). The three reactors were connected so that the reaction mixture overflowing from the upper reactor was conducted to the next reactor, the gas released from the rear reactor was blown into the main reactor, and the gas released from the main reactor was blown into the pre-reactor.

p-Xylene was filled in each of the reactors, and the temperature of the contents in the pre-reactor was elevated to 120° C. The temperatures of the contents in the main reactor and the rear reactor were elevated to 135° C.

When the inside of each of the reactors reached the predetermined point, about 81 g/hour of p-xylene was continuously fed into the pre-reactor while maintaining the above predetermined temperature. The reaction mixture which overflowed from the pre-reactor was fed to the main reactor, and the reaction mixture which overflowed from the main reactor was fed into the rear reactor.

On the other hand, chlorine gas was continuously fed to the rear reactor at a rate of 108 g/hour, and to the main reactor at a rate of 224 g/hour. Simultaneously, the gas released from the rear reactor was blown into the main reactor, and all the gas released from the main reactor, into the pre-reactor.

The reaction was performed under the irradiation of light while continuously feeding the liquids and gases into the reactors in this way.

The reaction mixture which overflowed from the rear reactor was conducted to a chlorine removing tower and contacted countercurrently with nitrogen gas. After removing chlorine gas, the reaction mixture was conducted to a reservoir.

After performing the reaction in this way for 72 hours, the reaction mixture in each of the reactors was analyzed by gas-chromatography. The results are shown in Table 4.

Table 4

| | Pre-reactor | Main reactor | Rear reactor |
| --- | --- | --- | --- |
| p-Xylene | 37.8 wt.% | 0.01 wt.% | — |
| α-Chloro-p-xylene | 44.8 | 0.4 | — |
| α,α-Dichloro-p-xylene | 11.6 | 0.1 | — |
| α,α'-Dichloro-p-xylene | 1.9 | 0.8 | — |
| α,α,α'-Trichloro-p-xylene | 2.8 | 4.8 | — |
| α,α,α',α'-Tetrachloro-p-xylene | | 5.9 | — |
| α,α,α,α',α'-Pentachloro-p-xylene | | 12.0 | — |
| α,α,α,α',α',α'-Hexachloro-p-xylene | | 73.5 | 97.2 wt.% |
| Other compounds * | 1.1 | 2.5 | 2.8 |

* Same as the footnote to Table 1.

In the same way, the reaction was performed for an additional 24 hours. During this time, 1974 g of p-xylene and 7995 g of chlorine gas were fed into the reactors. By causing the gas released from the prereactor to be absorbed by water, hydrochloric acid was separated from the organic matter, and 85 g of p-xylene was recovered. After removing chlorine dissolved in the reaction mixture, there was obtained 5472 g of a final reaction mixture. Gas-chromatographic analysis of this reaction mixture showed that it consisted of 97.3% by weight of α,α,α,α',α',α'-hexachloro-p-xylene, and traces of α,αλ,α,α',α'-pentachloro- and α,α,α',α'-tetrachloro-substitution products.

From the results obtained, it was found that 5324 g of α,α,α,α',α',α'-hexachloro-p-xylene was formed during the period of 24 hours after 72 hours, which corresponded to a yield of 92.8% based on the p-xylene feed, and a yield of 97.1% based on the p-xylene.

EXAMPLE 11

The same reactor as used in Example 8 was charged with toluene up to the overflow opening, and heated to elevate the temperature of the contents to 110° C. Then, about 100 g/hour of toluene and 154 g/hour of chlorine were continuously fed into the reactor with stirring under the irradiation of light, and the reaction was continuously carried out. Toluene had been pre-heated to 90°–100° C. prior to being fed into the reactor. Other procedures were almost the same as those used in Example 8.

In this way, the reaction was performed for 48 hours, and the reaction mixture was analyzed by gas-chromatography. It was found that the reaction mixture consisted of 96.8% by weight of benzotrichloride, 0.2% of benzalchloride, and 3.0% of a nuclearly chlorinated product and other by-products.

In the same way, the reaction was performed for an additional 20 hours, and during this time, 1992 g of toluene and 5515 g of chlorine were fed into the reactor, and 4192 g of a product was obtained. Analysis of the product showed that it consisted of 97.1% by weight of benzotrichloride, 0.2% of benzalchloride, and 2.7% by weight of other by-products consisting mainly of a nuclearly chlorinated compound and a resinous substance. The yield of the benzotrichloride was 96.3% based on the toluene.

EXAMPLE 12

The same reactors as used in Example 9 were used. The main reactor situated at the upper position was filled with mesitylene, and heated to elevate the temperature of the mesitylene to 140° C. Then, while maintaining the temperature of the mesitylene at 140° C., mesitylene and chlorine were continuously fed at a rate of about 64 g/hour and 374 g/hour, respectively, with stirring under the irradiation of light. The mesitylene had been preheated to 120°-130° C. prior to being fed to the reactors.

The reaction mixture which overflowed from the main reactor was conducted to the reactor situated at a lower position than the main reactor, i.e. the rear reactor. When the rear reactor was filled with the liquid, the contents were heated to 140° C., and the reaction was performed with stirring under the irradiation of light while blowing chlorine continuously into the reactor at a rate of 35 g/hour in the same way as in Example 9. The reaction was performed for 60 hours in this way, and then the reaction mixture was analyzed by gas-chromatography. The results are shown in Table 5.

Similarly, the reaction was performed for an additional 36 hours, and during this time, 2311 g of mesitylene was fed into the reactors, and chlorine was fed to the main reactor in an amount of 13.50 Kg, and to the rear reactor in an amount of 1267 g. After the reaction mixture was introduced into a chlorine-removing tower to remove chlorine dissolved therein, there was obtained 8223 g of a final product.

Table 5

|  | Main reactor | Rear reactor |
|---|---|---|
| Mesitylene | — | — |
| Monochloromesitylene |  | — |
| Dichloromesitylene |  | — |
| Trichloromesitylene | 1.1 wt.% | — |
| Tetrachloromesitylene |  | — |
| Pentachloromesitylene |  | — |
| Hexachloromesitylene | 2.4 | — |
| Heptachloromesitylene | 6.3 | — |
| Octachloromesitylene | 9.4 | — |
| Tris(Trichloromethyl)benzene | 76.2 | 95.7 wt.% |
| Others* | 4.6 | 4.3 |

*Same as the footnote to Table 1.

The chlorinated products shown in Table 5 were all side-chain chlorinated products.

The final product was analyzed and found to contain tris(trichloromethyl)benzene in a concentration of 96.3% by weight.

The yield of the tris(trichloromethyl)benzene was 95.7% based on the mesitylene.

What we claim is:

1. A process for the batchwise or continuous production of a perchloromethylbenzene, which comprises reacting a methylbenzene compound selected from the group consisting of compounds of the formula

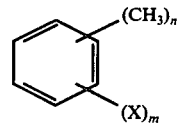

wherein
X is chlorine or bromine, $m$ is zero, 1 or 2 and $n$ is an integer of from 1 to 3,
and compounds of the above formula wherein the side chain methyl group is partially chlorinated, with chlorine under the irradiation of light containing ultraviolet rays, the initial stage of the reaction being carried out in the presence of said perchloromethylbenzene in the reaction system as a solvent, in an amount of (1) from 0.3 to 15 times the weight of the starting methylbenzene compound when the process is carried out in a batchwise manner or (2) in an amount of from 40 to 99% by weight of the reaction mixture when the process is carried out in a continuous manner.

2. The process of claim 1 wherein said reaction is carried out at a temperature of 50° to 180° C.

3. The process of claim 2 wherein the reaction temperature is 100° to 160° C.

4. The process of claim 1 wherein said methylbenzene is p-xylene or m-xylene.

5. The process of claim 1 wherein said methylbenzene is m-xylene.

6. The process of claim 1 wherein said reaction is carried out batchwise manner.

7. The process of claim 6 wherein the amount of chlorine used is at least 110% of the theoretical amount.

8. The process of claim 1 wherein said reaction is carried out in a continuous manner.

9. The process of claim 8 wherein said reaction is carried out using a main reactor and a rear reactor connected to each other in series, the majority of the perchlorination reaction is carried out in the main reactor, and the perchlorination reaction is completed in the rear reactor.

10. The process of claim 8 wherein said reaction is carried out using a pre-reactor and a main reactor connected to each other in series, the reaction in the pre-reactor is controlled so that the average number of chlorine atoms to be introduced into the side chain methyl groups of the methylbenzene, per molecule of methylbenzene, is not more than 2, and substantially all of the perchlorination reaction is carried out in the main reactor.

11. The process of claim 8 wherein said reaction is carried out using a pre-reactor, a main reactor and a rear reactor serially connected in this order to each other, the reaction in the pre-reactor is controlled so that the average number of chlorine atoms introduced into the side chain methyl groups of the methylbenzene, per molecule of methylbenzene, is not more than 2, the majority of the perchlorination reaction is carried out in the main reactor, and the perchlorination reaction is completed in the rear reactor.

* * * * *